United States Patent [19]

Burton et al.

[11] Patent Number: 5,181,952
[45] Date of Patent: * Jan. 26, 1993

[54] ROOT-GROWTH-INHIBITING SHEET

[75] Inventors: Frederick G. Burton, Stansbury Park, Utah; Dominic A. Cataldo, Kennewick; John F. Cline, Prosser, both of Wash.; W. Eugene Skiens, Wilsonville, Oreg.; Peter Van Voris, Richland, Wash.

[73] Assignee: Battelle Memorial Institute, Richland, Wash.

[*] Notice: The portion of the term of this patent subsequent to May 26, 2009 has been disclaimed.

[21] Appl. No.: 535,494

[22] Filed: Jun. 11, 1990

Related U.S. Application Data

[63] Continuation-in-part of Ser. No. 86,757, Aug. 18, 1989, abandoned, which is a continuation-in-part of Ser. No. 555,113, Nov. 23, 1983, Pat. No. 5,116,414, which is a continuation-in-part of Ser. No. 314,809, Oct. 26, 1981, abandoned, and a continuation-in-part of Ser. No. 314,810, Oct. 26, 1981, abandoned.

[51] Int. Cl.⁵ .................. A01N 33/06; A01N 33/18
[52] U.S. Cl. .................. 504/347; 71/DIG. 1; 71/64.11; 71/64.13; 47/9; 47/DIG. 10; 504/333
[58] Field of Search ............. 71/121, DIG. 1; 424/83; 47/9, DIG. 10

[56] References Cited

U.S. PATENT DOCUMENTS

| 3,384,993 | 5/1968 | Kane | 71/DIG. 1 |
| 3,551,192 | 12/1970 | Reinert | 424/83 |
| 3,592,792 | 7/1971 | Newland et al. | 47/9 |
| 3,891,423 | 6/1975 | Stanley et al. | 71/86 |
| 3,939,606 | 2/1976 | Vandemark et al. | 47/9 |
| 4,243,703 | 6/1981 | Palvarini et al. | 47/9 |
| 4,350,678 | 9/1982 | Palvarini et al. | 71/DIG. 1 |
| 4,360,376 | 11/1982 | Koestler | 71/DIG. 1 |

Primary Examiner—Carolyn Elmore
Assistant Examiner—Brian Bembenick
Attorney, Agent, or Firm—Joseph J. Hauth; Stephen R. May

[57] ABSTRACT

In accordance with this invention, a porous sheet material is provided at intervals with bodies of a polymer which contain a 2,6-dinitroaniline. The sheet material is made porous to permit free passage of water. It may be either a perforated sheet or a woven or non-woven textile material. A particularly desirable embodiment is a non-woven fabric of non-biodegradable material. This type of material is known as a "geotextile" and is used for weed control, prevention of erosion on slopes, and other landscaping purposes. In order to obtain a root repelling property, a dinitroaniline is blended with a polymer which is attached to the geotextile or other porous material.

15 Claims, 3 Drawing Sheets

ROOT-GROWTH-INHIBITING SHEET

The United States Government has rights in this invention under contract DE-AC06-76RLO 1830 between the United States Department of Energy and Battelle Memorial Institute.

This application is a continuation-in-part of application Ser. No. 86,757, filed Aug. 18, 1989 (abandoned), which is a continuation-in-part application of Ser. No. 555,113 filed Nov. 23 1983 (U.S. Pat. No. 5,166,414), which is in turn a continuation in part of applications Ser. Nos. 314,809 and 314,810, both filed Oct. 26, 1981 (both abandoned).

In the last three applications listed above, there are disclosed methods and articles for the inhibition of root growth particularly the exclusion of the roots from areas in which they are undesirable, e.g., waste burial sites underground pipelines, basements, sidewalks, or simply the boundaries between adjacent properties. The articles are formed of polymers, e.g., polyethylene, containing in admixture dinitroanilines, preferably N,N-di-n-propyl-4-trifluoromethyl 2,6-dinitroaniline, having the generic name trifluralin. Among the articles which are disclosed are pellets of cylindrical form about 9 mm in diameter and the same in length. These pellets are preferably distributed about 1 or 2 inches apart over the area which it is desired to protect. These pellets, containing about 25 percent by weight of trifluralin, have proven very satisfactory in use and have been shown by tests to have a probable effective life of 50 to over 100 years. Their disadvantage lies in the fact that to distribute them uniformly is a slow, laborious operation.

The dinitroanilines are classed as pre-emergence herbicides. They are applied to soils either prior to seeding of crops, or between the rows of established crops, but in either case before the unwanted weeds or grasses have emerged. On seed germination, they function to inhibit spindle formation in plants and thus mitosis in roots of newly germinating seeds. Thus, the reduction in root growth at the sensitive seed germination stage, prior to the time when sufficient reserves are stored within the young plant, results in the death of the germinating seed and/or seedling. When we refer to the "seedling stage", we mean this early stage when reduction in root growth is fatal to the plant. (The term "seedling" has other meanings in connection with trees, but we do not use the term in those senses.)

The common names and chemical identification of representative compounds are:
Trifluralin—α,α,α-trifluoro-2,6-dinitro-N,N-dipropyl-p-toluidine
Benfluralin—N-butyl-N-ethyl-2,6-dinitro-4(trifluoromethyl) benzenamine
Isopropalin—4-isopropyl-2,6-dinitro-N,N-dipropylaniline
Oryzalin—3,5-dinitro-$N^4$,$N^4$-dipropylsulfanilamide
Ethalfluralin—N-ethyl-α,α,α-trifluoro-N-(methylallyl)-2,6-dinitro-p-toluidine
Pendimethalin—N-(1-ethylpropyl)-2,6-dinitro-3,4-xylidine
Profluralin—N-(cyclopropylmethyl)-α,α,α-trifluoro-2,6-dinitro-N-propyl-p-toluidine Alternate names for these compounds which better show their relationship are:
Trifluralin—N-di-n-propyl-4-trifluoromethyl-2,6-dinitroaniline
Benfluralin—N-ethyl-N-butyl-4-trifluoromethyl-2,6-dinitroaniline
Isopropalin—N-di-n-propyl-4-isopropylmethyl-2,6-dinitroaniline
Oryzalin—N-di-n-propyl-4-sulfonamido-2,6-dinitroaniline
Ethalfluralin—N-ethyl-N-methyl-allyl-4-trifluoromethyl-2,6-dinitroaniline
Pendimethalin—N-(1-ethylpropyl)-3,4-methyl-2,6-dinitroaniline
Profluralin—N-(cyclopropylmethyl)-N-propyl-4-trifluoromethyl-2,6-dinitroaniline

SUMMARY OF THE INVENTION

In accordance with this invention, a porous sheet material is provided at intervals with bodies of a polymer which contain a 2,6-dinitroaniline. The sheet material is made porous to permit free passage of water. It may be either a perforated sheet or a woven or nonwoven textile material. A particularly desirable embodiment is a non-woven fabric of non-biodegradable material. This type of material is known as a "geotextile" and is used for weed control, prevention of erosion on slopes, and other landscaping purposes. In order to obtain a root repelling property, a dinitroaniline is blended with a polymer which is attached to the geotextile or other porous material.

The polymer containing the root repellant dinitroaniline may be distributed in various forms, e.g., as buttons or as continuous or other elongated beads. The choice of the specific mode of distribution depends to a large part on the life desired for the root repellency.

The effectiveness of the porous sheet barrier in inhibiting root elongation is controlled by the soil concentration of dinitroaniline adjacent to the barrier. This is regulated by the release rate of the dinitroaniline from the buttons, or beads. For buttons, spacing is generally of 1- to 2-inch centers. Elongated beads are arranged in regular patterns or spacing to produce a protective soil area. The dinitroaniline will slowly diffuse from the polymer with which it is mixed at a controlled rate, be adsorbed to the soil adjacent to the barrier, and thus establish a zone in which the concentration is such as to prevent further elongation or penetration of the roots.

Studies were made of pellets such as are described above, spaced on 1 to 2 inch centers above buried wastes. The root repelling zone was found, after 7 years burial, to extend from about 5 inches above the pellets to at least 3 inches below them. The sheet of the present case with buttons or beads having release rates similar to the pellets will provide a root repelling zone of similar extent.

At the same time the dinitroanilines, in the concentrations released by the polymers, do not translocate into other parts of the plants. They do not kill plants beyond the seedling stage and do not injure them, except that growth may be restricted by the inhibition of new root production.

DETAILED DESCRIPTION

Figure 1:
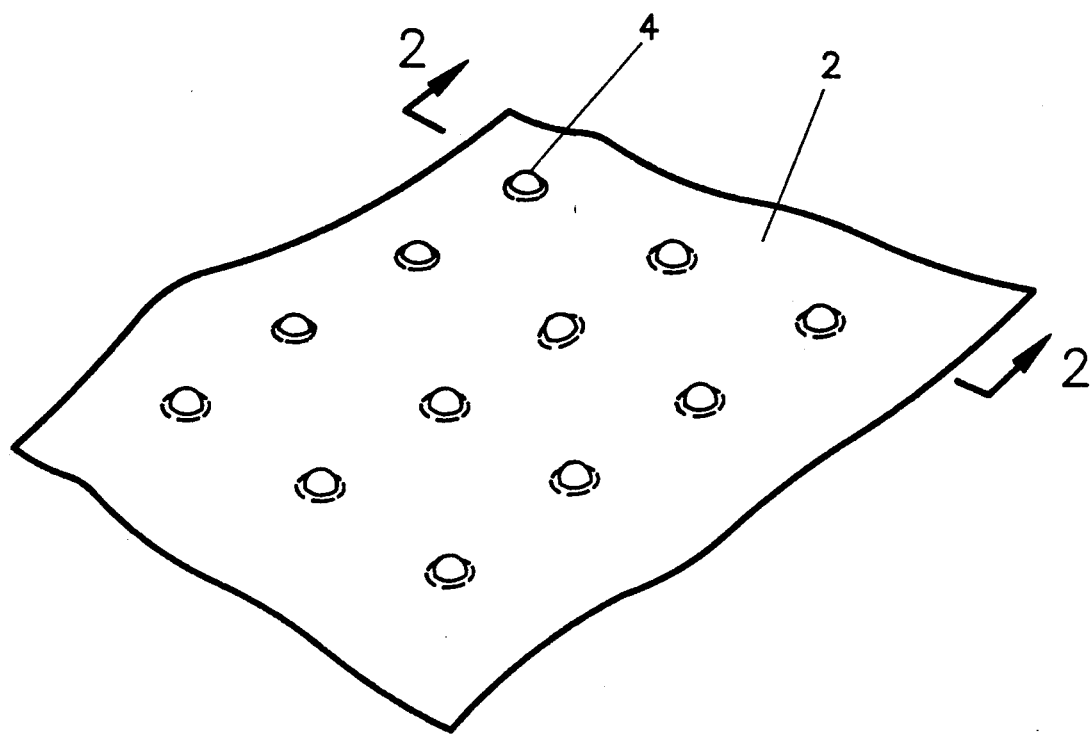
FIG. 1 is a perspective view of the embodiment employing small buttons of polymer.

In FIG. 1 we have shown a sheet of non-woven fabric formed of felted fibers of polyethylene or other thermoplastic material. Attached to it are buttons of polymer in which is mixed from 2 to 30 weight percent dinitroaniline, preferably trifluralin. Carbon black is usually added to improve retention of the dinitroaniline. The selection of the carbon black is important. It should have the maximum available surface area per gram and maximum adsorption capacity. The one which we have found best is sold under the commercial name Vulcan XC-72. The dinitroaniline and carbon black should be pre-blended before being mixed with the polymer. The buttons may be made from a polymer selected from the following list:

Polyethylenes (low density, linear low density, high density)
Polypropylene
Copolymers and blends of above polymers
Poly (vinylacetate)
Poly (ethylene vinylacetate)
Poly (ethylene acrylic acid)
Poly (ethylene ethylacrylate)
Polybutylene
Poly (acrylate-styrene-acrylonitrile)
Epoxy polymers
Polyamides
Polyesters (aromatic)
Polyurethanes
Silicone polymers Thermoplastic elastomers, which may be prepared from a number of monomers such as styrene block copolymers with butadiene or isoprene, polyether-esters or olefinics. Examples are those sold under the name "santoprene", e.g., the "dynamically vulcanized" mixture of thermoplastic polyolefins and vulcanized monoolefin copolymers disclosed in U.S. Pat. No. 4,130,535.

If an effective life of over five years is desired, the buttons or other bodies must be impervious to water. Either the polymer forming the bulk of the body must itself be water-impervious, or it must be coated with a water-impervious material. Polyethylene, which is our preferred material, is impervious to water, as are most of the polymers listed above.

We have found that different commercially available polyethylenes differ in suitability for our purpose. Those which we have found most suitable are Microthene 710-20 and Eastman A-435.

Figure 5:
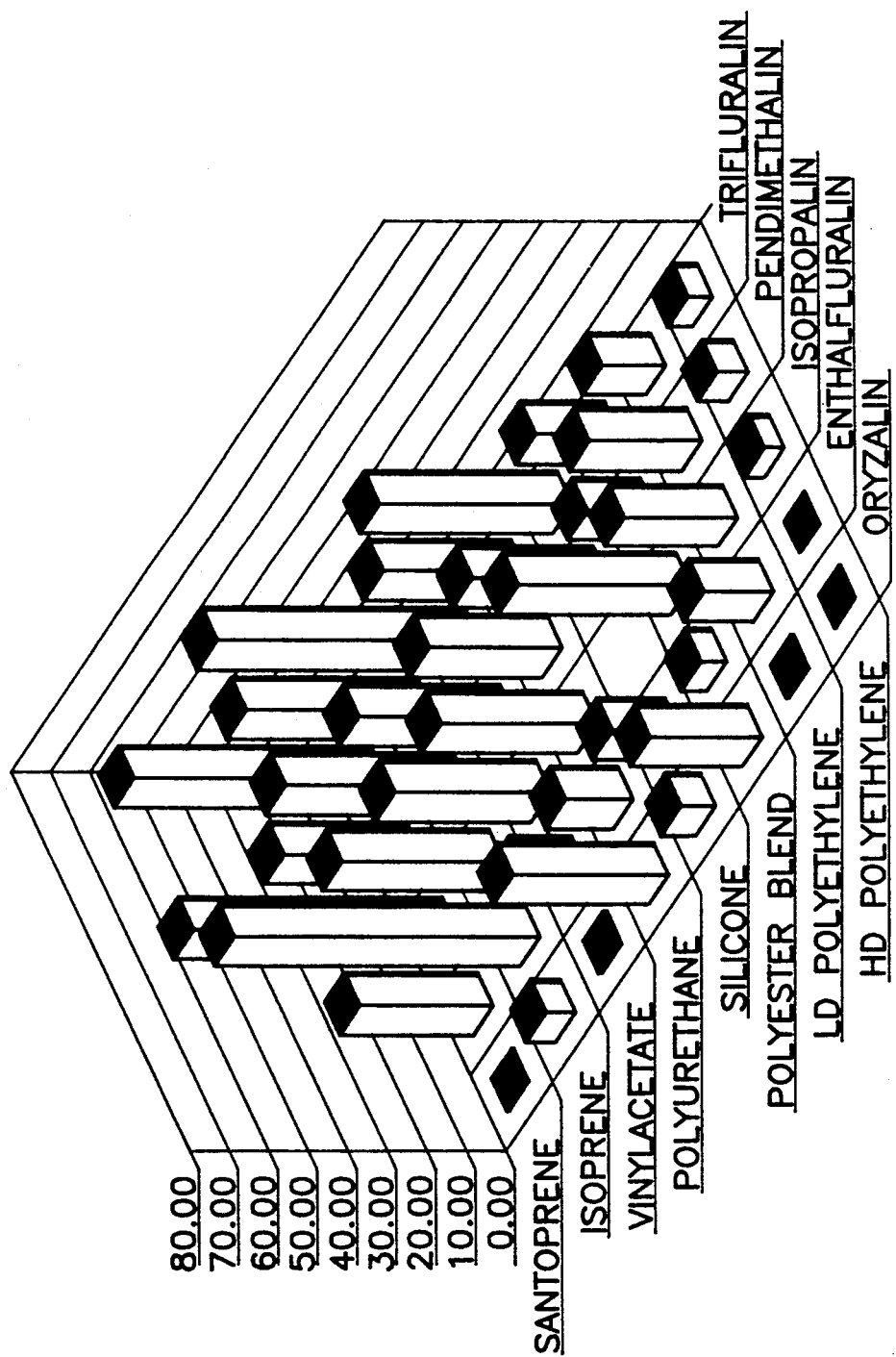
FIG. 5 is a graph showing the release rates for various polymer-dinitroaniline combinations.

The effective lifetime of the buttons or beads depends on their dimensions and the release rate of the herbicide from it at the prevailing temperature. FIG. 5 shows the release rates at 22° C. for various combinations of herbicide and polymer. The release rates are given in micrograms per pellet having a surface area of about 2.8 cm$^2$, as determined in vitro by continuous extraction with water containing 10% by volume methanol and 0.1% wetting agent. A method of calculation of effective lifetime is set out in the application of Cowan, et al., Ser. No. 303,770, filed Jan. 30, 1989 (U.S. Pat. No. 5,019,998), and assigned to the assignee of this application. As disclosed therein, comparisons of lifetimes based on actual experiments with buried polyethylene pellets with the lifetimes determined from in vitro data indicate that the latter should be multiplied by a factor of 1.5 to 2.4, depending on temperature, to give actual effective lifetimes under field conditions. In general, we find that those combinations shown in the graph as having values of about 5 to 25 are most satisfactory for use as the buttons or beads.

The buttons, 4, FIG. 1, are attached to the sheet, 2, by, e.g., adhesives or mechanical fasteners. A particularly desirable mode is by extrusion of a molten plastic mixed with the dinitroaniline onto or through the fabric and allowing it to cool in place. Desirably the buttons have an average diameter of ¼ to ⅜ inches and an average maximum thickness of ⅛ to ⅜ inches and spaced on 1- to 3-inch centers preferably not more than 2 inches. As stated above, they should contain from 2 to 30 percent dinitroaniline. Based on experimental results, polyethylene buttons of the ⅜-inch diameter and ⅛-inch thickness containing 25 weight percent trifluralin pre-blended with 25 weight percent carbon black (based on the polyethylene) will have an effective root repelling lifetime of at least 50 years and probably 100 years. Buttons of other sizes made of different polymers and/or containing different dinitroanilines will have different lives which may be varied according to the intended use. As may be expected, the use of smaller buttons and the use of smaller proportions of dinitroaniline will result in shorter lives, as will the use of dinitroaniline-polymer combinations from which the dinitroaniline diffuses more rapidly than does trifluralin from polyethylene.

While we have shown the buttons arranged in right angled rows, other distributions, e.g., in a diamond pattern, may be preferred in some cases.

Figure 2:
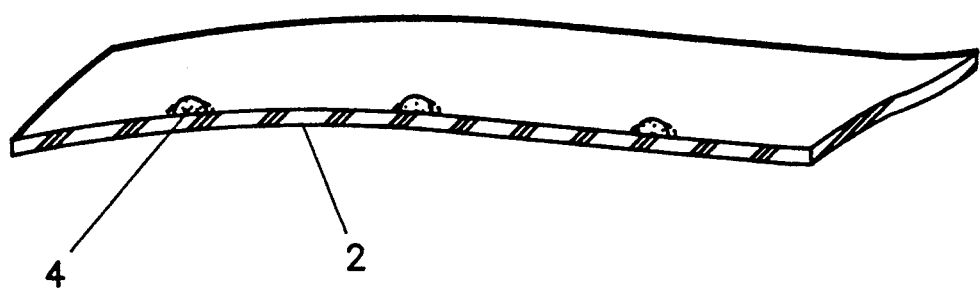
FIG. 2 is a cross section on the line 2—2 of FIG. 1.
Figure 3:
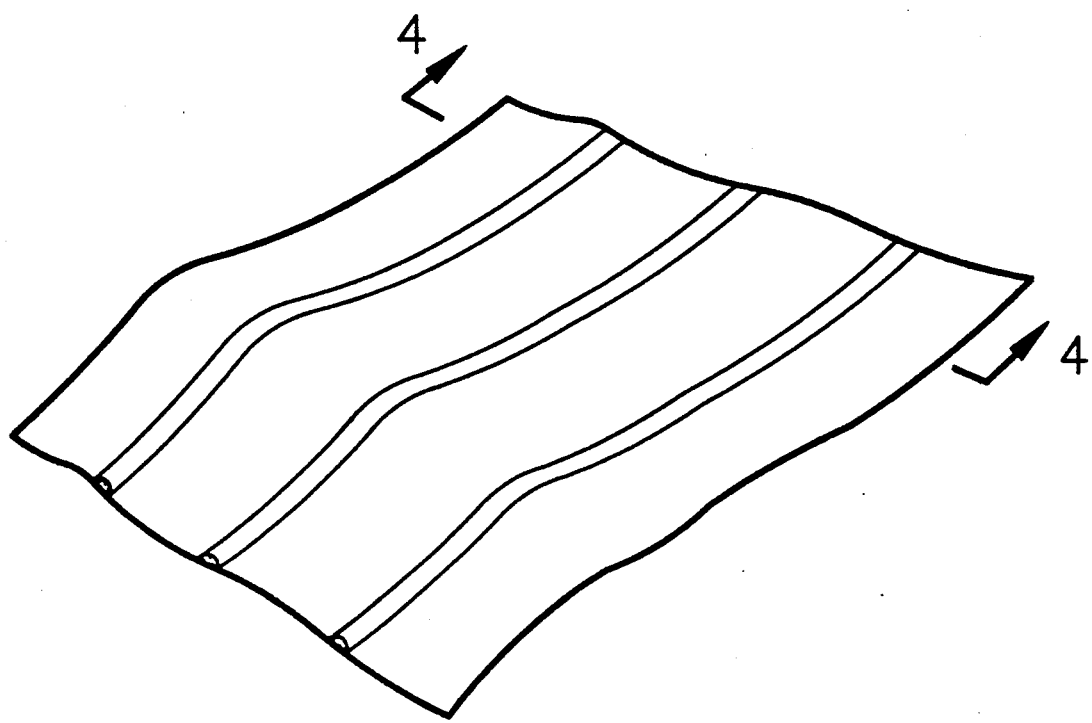
FIG. 3 is a plan view of the type employing continuous beads.
Figure 4:
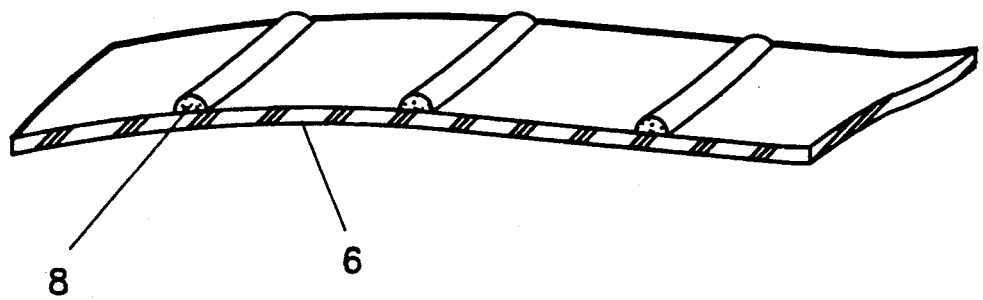
FIG. 4 is a section on the line 4—4 of FIG. 3.

In FIGS. 3 and 4 we show the use of elongated beads, 8, attached to the fabric, 6. These beads may be formed of the same materials and attached in the same manner as the buttons, 4, of FIGS. 1 and 2. They may have widths and thicknesses in the range of 1/16 to ¼ inch and should not leave gaps of more than 2 inches. Because they have a stiffening effect on the fabric, this embodiment is somewhat less flexible in use than the one having buttons shown in FIGS. 1 and 2. The beads need not be parallel, but may be arranged in other patterns.

While we have described certain embodiments in detail, it will be obvious to those skilled in the art that various changes can be made. We therefore wish our invention to be limited solely by the scope of the appended claims.

The embodiments of the invention in which a proprietary right or privilege is claimed are defined as follows:

1. A material for preventing entry of unwanted roots into a volume of soil, comprising a flexible sheet of water-permeable fabric carrying discrete spaced-apart bodies of a polymer containing a herbicidal dinitroaniline and carbon black, the concentration of said dinitroaniline in said bodies being from about 2 wt. % to about 30 wt. %, and the concentration of said carbon black being effective to retain and control the release rate of said dinitroaniline, said bodies being attached to said flexible sheet and distributed thereon in spaced-apart relationship such that when said sheet is buried in soil, said dinitroaniline will diffuse into the volume of soil at such a rate, and over such a period of time, as to exclude roots over a period of years without killing plants beyond the seedling stage.

2. A material as defined in claim 1 wherein said dinitroaniline is trifluralin.

3. A material as defined in claim 1, wherein said bodies are impervious to water.

4. A material as defined in claim 1, wherein said polymer is selected from the group consisting of polyethylenes, polypropylenes, copolymers and mixtures of polyethylenes and polypropylenes, polyvinylacetate, poly(ethylene vinyl acetate), poly(ethyleneacrylic acid), poly(ethylene ethyl acrylate), polybutylene, poly(acrylate-styrene-acrylonitrile), epoxy polymers, polyamides, aromatic polyesters, polyurethanes, and silicone polymers.

5. A material as defined in claim 1, wherein said dinitroaniline is selected from the group consisting of trifluralin, benfluralin, isopropalin, oryzalin, ethalfluralin, pendimethalin, and profluralin.

6. A material as defined in claim 4, wherein said dinitroaniline is selected from the group consisting of trifluralin, benfluralin, isopropalin, oryzalin, ethalfluralin, pendimethalin, and profluralin.

7. A material as defined in claim 1, wherein said sheet material is of a non-biodegradable composition.

8. A material as defined in claim 2, wherein said sheet material is of a non-biodegradable composition.

9. A material as defined in claim 1, wherein said sheet is a non-woven fabric of a non-biodegradable polymeric composition.

10. A material as defined in claim 2, wherein said sheet is formed of non-woven fabric of a non-biodegradable polymeric composition.

11. A material as defined in claim 1, wherein said polymer is in the form of buttons attached to and distributed over said sheet.

12. A material as defined in claim 2, wherein said polymer is in the form of buttons attached to and distributed over said sheet.

13. A material as defined in claim 9, wherein said polymeric composition is polyethylene.

14. A material as defined in claim 6, wherein said buttons are $\frac{1}{4}$ to $\frac{3}{8}$ inches in diameter and $\frac{1}{8}$ to $\frac{3}{8}$ maximum thickness.

15. A material as defined in claim 5 wherein said buttons are spaced apart an average of 1 to 3 inches.

* * * * *